United States Patent [19]

Beardwood

[11] Patent Number: 5,576,481
[45] Date of Patent: Nov. 19, 1996

[54] METHOD AND APPARATUS FOR DETECTING MICROBIOLOGICAL FOULING IN AQUEOUS SYSTEMS

[75] Inventor: Edward S. Beardwood, Aurora, Canada

[73] Assignee: Ashland, Inc., Columbus, Ohio

[21] Appl. No.: 538,304

[22] Filed: Oct. 2, 1995

[51] Int. Cl.⁶ .................................................. G01N 30/62
[52] U.S. Cl. .............................. 73/61.62; 324/700; 73/86
[58] Field of Search .............................. 73/61.41, 61.62, 73/86; 324/691, 692, 693, 700, 71.2

[56] References Cited

U.S. PATENT DOCUMENTS

| Re. 33,346 | 9/1990 | Knudsen et al. | |
|---|---|---|---|
| Re. 33,468 | 12/1990 | Brindak. | |
| 3,399,133 | 8/1968 | Gerdes et al. | 73/61.41 |
| 3,848,187 | 11/1974 | Rohrback et al. | 324/700 |
| 4,800,165 | 1/1989 | Oka et al. | 324/700 |
| 5,353,653 | 10/1994 | Watanabe et al. | 73/86 |
| 5,446,369 | 8/1995 | Byrne et al. | 324/700 |
| 5,448,178 | 9/1995 | Chen et al. | 324/700 |

OTHER PUBLICATIONS

Model CorrDATS™ Corrosion and Deposit Monitoring System—brochure, 2 pages.
Herman et al., The Use Of A Novel Portable Fouling And Corrosion Monitor-Recorder In Industrial Cooling Water Systems, 40th Annual Meeting International Water Conference Pittsburgh, PA, Nov. 1, 1979, 13 pages.
Corrosion 93, Oct. 19–21, 1993, vol. 2, Wed. Oct. 20, 1993, 7 pages.

*Primary Examiner*—Hezron E. Williams
*Assistant Examiner*—Jay L. Politzer
*Attorney, Agent, or Firm*—Pollock, Vande Sande & Priddy

[57] ABSTRACT

A method of detecting microbiological fouling in an aqueous system. The method includes determining a baseline corrosion rate. A corrosion rate is continuously monitored. A change in the corrosion rate is measured. A maximum corrosion rate is measured. A baseline fouling factor is determined by measuring and monitoring parameters of a fluid in the aqueous system. An increase in fouling factor over the baseline is determined. A change in the corrosion rate is integrated with respect to time over an interval of from a time of the determination of the baseline corrosion rate to a time that the maximum corrosion rate occurs. A change in the fouling factor is integrated with respect to time over an interval from a time of the determination of the baseline fouling factor to a time of the determination of the increase in fouling factor. The fouling factor and the corrosion rate are compared to determine if the fouling is microbiological.

21 Claims, 7 Drawing Sheets

5,576,481

METHOD AND APPARATUS FOR DETECTING MICROBIOLOGICAL FOULING IN AQUEOUS SYSTEMS

FIELD OF THE INVENTION

The invention relates to a process and apparatus for testing fluids to detect microbiological fouling, and more particularly, to a process and apparatus for the in-situ testing and generation of data indicating microbiological fouling and a method for processing this data to determine whether microbiological fouling exists and the degree to which it exists. The invention also relates to a process for detecting and controlling microbiological fouling.

BACKGROUND OF THE INVENTION

Microbiological fouling has long been a problem with industrial aqueous systems. Aqueous industrial systems in which microbiological fouling can be a problem including industrial cooling water systems, in particular. However, microbiological fouling may be present and cause problems in any aqueous containing system.

Microbiological fouling may result from the presence of any of a variety of organisms in an aqueous system. Among the organisms that are important in microbiological fouling are a variety of algae, fungus, mold, and a variety of planktonic bacterial organisms. Such organisms may be introduced to aqueous industrial systems and intake water used in the system, from the environment, such as from the air, or from other process inleakage contamination sources, which could include, for example, an input of a component of foreign composition into the system or the introduction of contaminated equipment into a system.

Bacteria form a major component of microbiological fouling in aqueous systems. Bacteria can grow in almost any environment. Bacteria are loosely classified according to the environment in which they typically grow. Bacteria which are typically associated with microbiological fouling include anaerobic, facultative anaerobic, and aerobic bacteria. Anaerobic bacteria are particularly significant in microbiological fouling.

The production of a microbiological fouling film on a surface in a cooling system typically begins with the adsorption of an organic or inorganic layer on a surface of the aqueous system. Typically, the organic or inorganic layer has some nutritional value to microorganisms potentially forming a fouling film on the surface. The layer may nourish the microorganisms as well as facilitate their attachment.

Having a physical attachment point as well as a nutritional source provides a favorable location for the microorganisms to form a colony. Typically, less efficient motile organisms will drop out of the water first and attach themselves to the surfaces prepared with the nutritional layer. If the surface has been previously colonized and remnants of former colonies remain on the surface, the attachment of new organisms on a layer of a surface of a cooling system can be as rapid as fifteen minutes.

Upon attachment, the sessile microorganisms typically begin to produce polysaccharides or glycocalyx which help to secure their attachment to the nutritional layer and the surface upon which the layer is attached. Many microorganisms also produce glycocalyx which help to entrap nutrients and debris. Such glycocalyx can promote survival in low nutrient fluids and also enhance the microorganisms resistance to microbicide attack.

Often, an upper layer of aerobic bacteria is established on a surface, such as a metal surface of a heat exchanger, of the aqueous system first. The layer of aerobic bacteria typically provides a protective, nutrient, pH and temperature rich environment to allow lower oxygen tolerant bacteria to grow. Anaerobic bacteria may be transported into the aqueous system as spores and then encapsulated in a layer of the biofilm during the adhesion phase of the layer of aerobic bacteria.

A microbiological fouling layer may include a number of bacteria arranged in a colony having a complex structure. Such a colony may include a symbiotic matrix of acid producing, fermenting, iron oxidizing, and sulphate reducing bacteria. These bacteria may be protectively housed by a capping layer of glycocalyx/slime producing bacteria. The glycocalyx/slime layer may mediate the flow of organic, inorganic, and dissolved gas between the aqueous and gelatinous phases of the colony. However, the layer of bacteria may take any form and include any type of bacteria.

The deposition, attachment, and initial growth of a microorganism layer often is complete within about three to about five days. A mature colony of microorganisms, typically at least eight to ten cells thick, may be formed within about ten to about fourteen days. A microbial layer of this thickness may be sufficient to deplete the oxygen in the biofilm. Upon oxygen depletion, the conditions in the biofilm become favorable for the growth of anaerobic microorganisms, typically bacteria, to grow and thrive.

In typical industrial systems, a biofilm of microorganisms may continue to grow up to about 200 cells in thickness containing a maximum coverage to within about 3.5 to about 4 weeks. Such films may have a thickness of from about 300 up to about 500 microns. Even thicker films have also been reported. The thickness of the film may be increased, depending upon the amount of debris entrapped in the film and also the velocity of the water within the system. Such films typically include about 80%–98% water. A biofilm of just about 0.004 inch thick has been shown to have about one-quarter of the thermal conductivity of calcium carbonate scales of equivalent thickness. Accordingly, it can be seen how damaging a biofilm can be in relation to the functioning of an aqueous system.

Among the problems associated with microbiological fouling are a loss of efficiency, corrosion of parts of aqueous systems, an increase in friction in water flowing through the system and a resulting decrease in efficiency and increase in required energy to move water through the system, as well as an increase in slime and inorganic deposition. An increase in material in the aqueous system can also decrease the efficiency of the system and clog the system by taking up volume within the system.

Furthermore, even the first layer of bacteria or other microorganisms may influence the electrochemical kinetics of oxygen reduction. Whether in the initial stages of development or further developed, a microbiological fouling layer can cause a drop in the heat transfer coefficient or, in other words, a reduction in the efficiency of a heat exchanger in an aqueous cooling system. Microbiological films may also cause local increases in corrosivity that can result in premature failures of components of a cooling system or any other aqueous system.

Bacteria may also consume inorganic and/or organic nitrogen and phosphate base inhibitors. Additionally, the bacteria can affect corrosion by metabolizing inorganic or organic matter and producing corresponding acids through either respiration or fermentation, respectively. Formation of concentration cells from entrapment of corrosive ions and biofilm uptake by bacteria may also effect corrosion.

In addition to the above problems, bacteria can also effect the corrosion of surface in aqueous systems by anodic depolarization through noble metal deposition. Bacteria may also effect anodic depolarization through chelation uptake of the corroded metal by exopolymers in the biofilm. Furthermore, the bacteria may promote corrosive anaerobic bacterial growth through oxygen depletion. Acid producing bacteria may selectively dissolve zinc, magnesium, and calcium, resulting in cathodic corrosion control loss.

As stated above, other microorganism may be involved in microbiological fouling. For instance, cathodic depolarization may also take place due to daytime release of oxygen by algae. Also, fungi may dissolve protective coatings on surfaces in aqueous systems. Accordingly, in view of the above, it can be seen that bacteria are only one source of problems regarding microbiological fouling in aqueous systems and that other organisms can play a significant role in such fouling.

The detection and control of microorganisms has been well understood and practiced over the years. However, the fouling and corrosion associated with microbial growth continues to be an area of concern. According to normal industry practice, fouling due to microorganism growth is not detected until long after a reduction in heat transfer efficiency in cooling systems has occurred. However, by this time, a typical cooling system has been operating inefficiently for a long time and microbial growth is well advanced.

According to one method of detecting microbiological fouling, the measurement of a drop in dissolved oxygen on a probe membrane when a nutrient sugar is injected is indicative of microbiological fouling activity, provided further oxygen drop occurs upon subsequent nutrient injections. If no further oxygen occurs, then the fouling may be of the non-viable chemical type.

Another known method of detecting microbiological fouling is an electrochemical method that utilizes a probe that is cathodically polarized for a short period of time each day. However, with this method, measurements of generated current prior to polarization remain flat, without increases, if biofilms are not present. Further, according to this known method, measurements of the applied current prior to the end of the cathodic polarization will not increase with time if biofilms are not present. However, the presence of biofilms will be revealed by an increase both in applied and generated currents with respect to time from a base line value. Employing this method, detection times have varied from about 12 days on bench tests to about 14 to about 50 days in field tests, with a lag time of detection about 2.5 hours. This method does not provide information concerning loss of heat exchange performance.

Another electrochemical method merely employs the measurement of cathodic current and assumes the increase in cathodic current is due to microbial activity. Although at least some correlation between an increase in cathodic current and microbial activity exists, any degree of certainty that the change in current corresponds to biofouling requires that a peak current be reached and then a decline in current must occur.

These current changes have also been manually correlated to a biofilm build-up. The addition of a microbicide revealed a reduction in cathodic current that proved that the cathodic current was derived from microbiological activity. Unfortunately, no real time continuous fouling and/or tracking ability existed to allow for interpretation and/or differentiation of the film formed and whether it was actually microbiologically derived.

Once a fouling layer is detected and determined to be microbiological in nature, methods are used to control and eliminate the organisms responsible for the fouling. A variety of methods may be used to control microbial growth. Such methods may include changes to the conditions within the aqueous system and/or use of compounds having a microbicidal effect.

Changes to the environment within the aqueous system may include any change that creates an environment unfavorable for the existence of microorganisms. For example, it is well known that microbiological organisms in aqueous systems may be controlled by thermal shocks to the system.

Typically, the treatment used is tailored to the microbe(s) implicated in the fouling. The specific organisms involved in the microbiological fouling in any system may be cultured using typical culture methods. For instance, water may be sampled and cultures grown from the water. Surfaces within the system may be swabbed and the swabs cultured. Tests may be performed to determine the efficacy of various microbicides on the cultured organisms. A treatment plan may then be worked up using one or more microbicides.

According to one treatment protocol, the organisms causing microbiological fouling of aqueous systems are controlled using a variety of microbicides. For instance, microbicides such as chlorine or other known biocides may be injected into the system to control growth of microbiological organisms. The specific microbes requiring control affect the selection and method of application of the microbicides used.

A plurality of microbicides may be used simultaneously to obtain an additive or synergistic effect. Multiple microbicides may also be used to obtain more favorable results, particularly in using multiple microbicides having different methods of action on the microbes involved.

Although methods of detection of microbiological fouling are known, these methods suffer from shortcomings such as inefficiency, slowness, and uncertainty. Irreversible corrosion damage and operating problems may result from the delay in detecting microbiological fouling. Delay in detecting the problem may lead to, among other things, processing delay in the process being carried out by the aqueous system affected, inefficiency in the aqueous system, ineffectiveness of the system, and a loss of time, money, and energy.

SUMMARY OF THE INVENTION

In view of the above, it is an object of the present invention to provide a method of analysis of data monitored or derived from aqueous systems to provide detection of microbiological fouling problems long before changes in the bulk recirculating water alerts the operator of a problem.

Another object of the present invention is to provide an apparatus for monitoring various characteristics of aqueous systems to detect microbiological fouling.

A further object of the present invention is to allow implementation of an antibiological foulant protocol substantially simultaneously with detection of microbiological fouling to quickly reduce and/or eliminate microbiological fouling.

Another further object of the present invention is to provide a method and apparatus for functionally differentiating between microbiological fouling and inorganic and organic fouling.

These and other objects of the present invention are achieved by the present invention, which is a method of detecting microbiological fouling in an aqueous system. The method includes the step of determining a baseline corrosion rate by utilizing linear polarization resistance in the aqueous system. Corrosion rate is continuously monitored utilizing linear polarization resistance in the aqueous system. A change in the corrosion rate is measured utilizing linear polarization resistance in the aqueous system. A maximum corrosion rate is measured utilizing linear polarization resistance in the aqueous system. A baseline fouling factor is determined by measuring and monitoring parameters of a fluid in the aqueous system. An increase in fouling factor over the baseline fouling factor is determined. A change in the corrosion rate is integrated with respect to time over an interval of from about the time of the existence baseline corrosion rate to about the time of the occurrence of a maximum corrosion rate. Change in the fouling factor is integrated with respect to time over an interval from about the time of the occurrence of a baseline fouling factor to about the time of the detection of an increase in fouling factor. A relationship between the fouling factor and the corrosion rate is calculated to determine if the fouling is microbiological.

The present invention also relates to a method for determining whether fouling is microbiological in nature and carrying out a treatment protocol to eliminate the source of the microbiological fouling. The method includes the step of determining a baseline corrosion rate utilizing linear polarization resistance in the aqueous system. Corrosion rate is continuously monitored utilizing linear polarization resistance in the aqueous system. A change in the corrosion rate in measured utilizing linear polarization resistance in the aqueous system. A maximum corrosion rate is measured utilizing linear polarization resistance in the aqueous system. A baseline fouling factor is determined by measuring and monitoring parameters of a fluid in the aqueous system. An increase in fouling factor over the baseline fouling factor is determined. A change in the corrosion rate is integrated with respect to time over an interval of from about the time of the occurrence of a baseline corrosion rate to about the time of the occurrence of a maximum corrosion rate. Change in the fouling factor is integrated with respect to time over an interval from about the time of the occurrence of a baseline fouling factor to about the time of the detection of an increase in fouling factor. A relationship between the fouling factor and the corrosion rate is calculated to determine if the fouling is microbiological. The protocol may include administering a treatment to the aqueous system, said treatment including at least one member being selected from the group consisting of adding an effective amount of at least one compound having a biocidal effect, and/or altering the physical environment within the aqueous system to create conditions unfavorable to the organisms involved in the fouling.

The invention is also related to an apparatus for carrying out the method of the invention. The apparatus includes means for measuring cathodic current of a solution. Accordingly, the apparatus includes at least one pair of electrodes positioned in the aqueous system. A measurer measures current flowing between the electrodes. Monitors and measurers monitor and measure conditions including corrosion rates, fouling factors and heater rod test section effluent flow within the aqueous system. A processor processes data representing the measured corrosion rates, fouling factors, and heater rod section effluent flow.

Still other objects and advantages of the present invention will become readily apparent those skilled in this art from the following detailed description, wherein are only the preferred embodiments of the invention are shown and described, by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

DETAILED DESCRIPTION OF VARIOUS AND PREFERRED EMBODIMENTS

Figure 1:
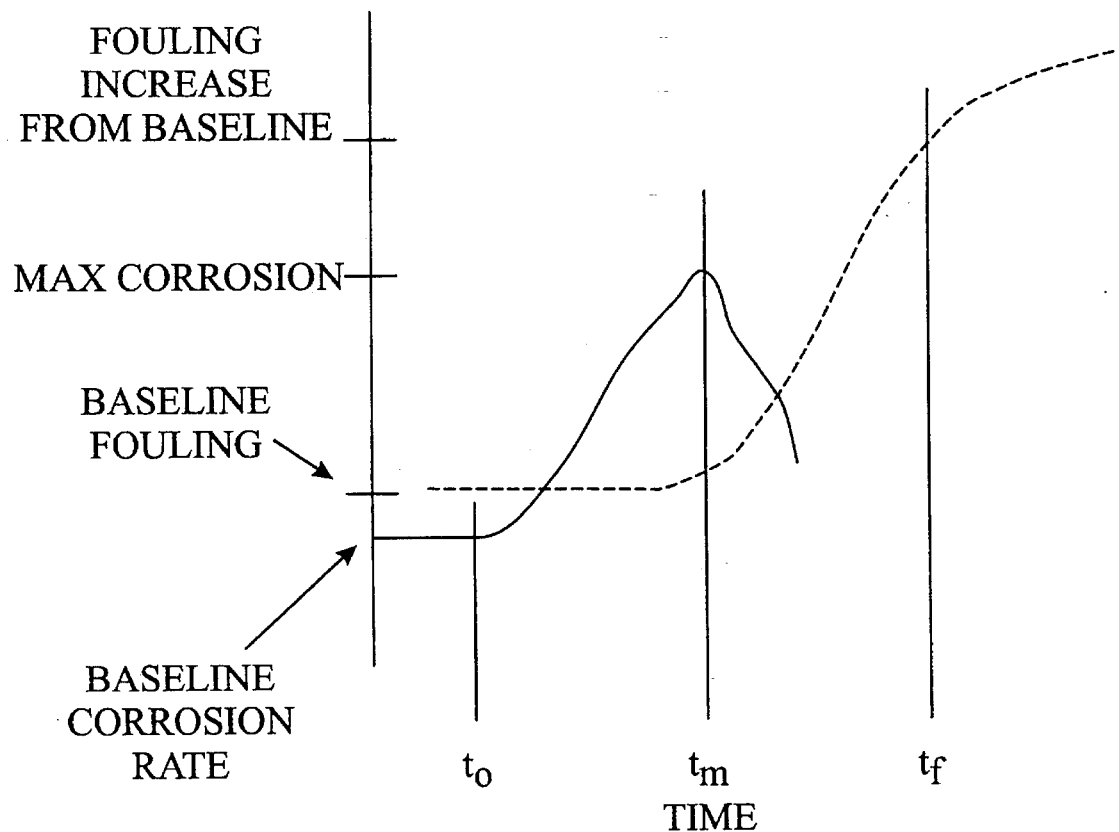
FIG. 1 represents a generalized graph of fouling factor and corrosion with respect to time.

The present invention provides a state of the art detection, apparatus and method for determining the presence of microbiological film growths. The linear polarization resistance reading or value is affected by either dissolved oxygen reduction or electrochemical detection of oxygen reduction at the cathode. Both methods of determining whether microbiological fouling is occurring relate to fouling (film formation) as it relates to microbiological activity rather than inorganic fouling. Preferably, unlike known methods and apparatuses, the present invention may permit virtually instantaneous detection of microbiological fouling.

An apparatus according to the present invention may include a system according to U.S. reissue patent 33,468, to Brindak, issued Dec. 4, 1990, for *Process and Apparatus for Testing Fluids for a Fouling and Anti-fouling Protocol*. Alternatively, the present invention may include an apparatus according to U.S. reissue patent 33,346, to Knudsen et al., issued Sep. 5, 1990, for *Process and Apparatus for Testing Fluids for a Fouling*. The entire disclosures of these two are hereby incorporated by reference. Examples of such systems include a P.U.L.S.E. Analyzer or an ONGUARD CFM 1100 Monitor, both of which incorporate Rohrback Casasco CORRATOR corrosion monitors, are produced and marketed by Ashland Chemical Company, Drew Industrial Division of Boonton, N.J. For treating the aqueous system to control the growth of microorganisms involved in the microbiological fouling, an Ongaurd Control System, produced and marketed by Ashland Chemical Company, Drew Divisions of Boonton, N.J., may be used.

Utilizing an apparatus according to either of these two patents allows for continuous detection of fouling and differentiation between non-viable chemical fouling and microbiological fouling. The systems may include at least one pair of electrodes and a device for applying current to the electrodes and measuring current flow in order to calculate corrosion rates. The systems may also include a heater rod and apparatus for measuring fouling factors as defined in U.S. Pat. No. 4,339,945, reissued as U.S. reissue patent 33,346, to Knudsen et al. The system may also include means for measuring oxidation-reduction potential (ORP), depending upon whether the device and method carry out detection alone or they also automatically mitigate detected microbiological fouling.

Preferably, a device employed according to the present invention includes a processor for processing data. As described herein, the data may include measured corrosion rates, fouling factors, and flow, among other parameters. Preferably, with a manual method of utilizing this process, the data will be fully developed. Incorporating a process of measuring the above-listed variables into a control system, such as one of the commercial models listed above, may permit a more rapid response to developing data indicative of microbiological fouling. Incorporating the process into the control system preferably includes utilization of a knowledge-based integrated intelligence operating system. An integrated intelligence system has the ability to continuously analyze differential changes in fouling factor and corrosion rate. Successful treatment of a system, aqueous or otherwise, may be confirmed by change in the fouling factor (AFF) versus changes in the corrosion rate measured as $\Delta$mils per year (mpy). The successful treatment may also be further confirmed with changes in the redox potential, thus permitting a secondary check for termination of treatment. The apparatus typically also includes a heat transfer or heater rod section.

Additionally, an apparatus for carrying out methods of the present invention preferably combines linear polarization resistance (LPR) measurement with an AC method for resistance compensation to provide a more accurate measure of corrosion current. Such an apparatus operates based at least partially on the understanding that the corrosion rate is directly proportional to corrosion current density.

When a metal specimen is exposed to a corrosive environment both oxidation and reduction processes occur on the surface of the metal. Typically, the metal is oxidized (corrosion) and either the solvent or oxygen is reduced. If it were possible to measure the electron flow due to metal oxidation, then the corrosion current and, therefore, the corrosion rate could be determined directly. However, only the net external current can be measured. Additionally, at open circuit, in other words, the normal condition, the oxidation and reduction reactions occur at the same rate. That means that the net electron transfer and, therefore, the net external current is zero.

Polarization resistance, $R_p$, of a corroding electrode is defined as the slope of the potential E versus current density i plotted at the corroding potential $E_{corr}$[1], as defined by the following equation:

$$R_p = \delta(\Delta E)\delta i, \text{ as } E \to 0 \tag{I}$$

[1]American Society for Testing and Materials (ASTM) Book of Standards, Volume 3.02, 1986, Standard Practice Designation G59-78 (Reapproved 1984). The entire contents of which are hereby incorporated by reference.

In this equation, $\Delta E = E - E_{corr}$ is the polarization from the corrosion potential and $\delta i$ is the current density corresponding to a particular value. M. Stern and A. C. Geary[2], in 1957, showed that for a corroding system the following equation applies:

$$\delta(\Delta E)/\delta i = R_p = b_a b_c / 2.3 i_{corr}(b_a + b_c) \tag{2}$$

[2]M. Stern and A. L. Geary, "Theoretical Analysis of the Shape of Polarization Curves," Journal of the Electrochemical Society, Volume 104, 1957, pp. 56–63. The entire contents of which are hereby incorporated by reference.

In this equation, $b_a$ and $b_c$ represent the electrochemical anodic and cathodic Tafel slopes, respectively, in units of volts. The equation can be simplified by combining the constants, resulting in the following equation:

$$R_p = B/i_{corr} \tag{3}$$

In this combined equation, $B = b_a b_c / 2.3(b_a + b_c)$.

For most construction metals in corrosive water solutions, B has a value of approximately 0.0275 volt. Therefore, if $R_p$ can be measured, $i_{corr}$ can be calculated by using Equation (3), above.

Corrosion current density, $i_{corr}$, is related to corrosion rate by Faraday's Law. The relationship is as follows:

$$C_r = K \times (AW)/FnD \times i_{corr} \tag{4}$$

According to this relationship, K is the constant determined by the measurement units selected, (AW) is the atomic weight of the metal, F is the Faraday constant of 96,494 coul./eq. mole, n is the number of electrons released by each metal atom when it oxidizes, sometimes called the valence change, and D is the metal density.

In practice, the LPR method involves measurement of the polarization resistance of a metal electrode which closely matches the material of construction, such as a pipe or vessel, for which corrosion rate information is desired. Because single electrode potentials cannot be measured, a second electrode is required to complete the measuring circuit. Since the two electrodes are selected to be virtually identical, it may be assumed that the polarization resistances at the metal-liquid interfaces of the two electrodes are nearly equal.

In the implementation of the polarization resistance method the solution resistance of the environment introduces a measurable error when its magnitude is significant compared to the polarization resistance. Recently, Haruyama and Tsuru[3] developed an AC technique to automatically correct for the effects of this solution resistance.

[3]S. Haruyama ant T. Tsuru, "A Corrosion Monitor Based On Impedance Method", Electrochemical Corrosion Testing, American Society for Testing and Materials, F. Mansfeld and U. Bertocci, Editors, ASTM STP727, Houston, 1981, pp. 167–186. The entire contents of which are hereby incorporated by reference.

Figure 7:
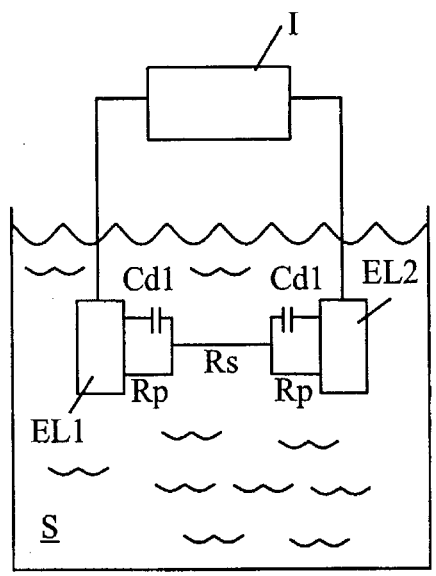
FIG. 7 represents a schematic diagram of an embodiment of an apparatus that may carry out measurements employed in methods according to the present invention.

A simplified diagram of a two-electrode probe immersed in a flowing water solution is shown in FIG. 7. In FIG. 7, EL1 and EL2 represent electrodes, S represents a solution, $R_p$ represents polarization resistance, Cam represents capacitance of a double layer existing at an interface between the metal electrodes EL1 and EL2 and the solution S, $R_s$ represents the electrolytic resistance of the solution between the electrodes, and I represents instrumentation in the apparatus for sensing, measuring, analyzing, calculating, and other functions.

In a typical apparatus for carrying out methods of the invention, the value of $R_p$ is determined by making two electrical measurements: (1) a low-frequency measurement, wherein $C_{d1}$ impedance is very large as compared to $R_p$; and (2) a high-frequency measurement, wherein $C_{d1}$ impedance is very small as compared to $R_p$. At the low frequency measurement, $$R_{tf} = [\delta(\Delta E_{tf})]/(\delta i_{tf}) = 2R_p + R_s \tag{5}$$

At the high-frequency measurement, $$R_{hf}=[\delta(\Delta E_{hf})]/(\delta i_{hf})=R_s \quad (6)$$

By subtraction of the two measurements, $$R_{lf}-R_{hf}=2R_p+R_s-R_s=2R_p \quad (7)$$

Transposing equation (3) and combining it with equation (7) results in the following:

$$i_{corr}=B/R_p=2B/(R_{lf}-R_{hf}) \quad (8)$$

For an iron electrode with an electrode area of 5cm², assuming B=0.0275 volt and using equations (4) and (8), the corrosion rate as a function of the measured resistances per unit area (ohms.cm²) is expressed as:

$$C_r[mpy]=25,000/(R_{lf}-R_{hf}) \quad (9)$$

Equation (9) may be used to calculate the corrosion rate of iron alloys, when the corrosion rate is expressed in mils per year (mpy). If mm/year readout is selected, the $C_r$ value calculated by Equation (9) is multiplied by 0.0254. If electrodes of other elements or alloys are used, the $C_r$ value in mpy, calculated using Equation (9), is multiplied by a multiplier factor, which can be implemented as a panel-selectable multiplier.

For further detail concerning the calculation and/or definition of any of the above defined equations and/or variables, see the section VARIABLES AND EQUATIONS, below.

The present invention also includes methods of detecting microbiological fouling in an aqueous system. Once the fouling is detected and determined to be microbiological, the present invention may also include a process of determining a treatment protocol to be used to control the fouling and carrying out the treatment.

According to a method of the present invention, the detection of microbiological fouling can be obtained by co-integrating linear polarization resistance (LPR) or cathodic current and fouling factors with respect to time. It will be seen from the on-line/real world monitoring of an operating system that results can be obtained that closely approximate bench laboratory tests. The continuous surveillance provides detection as follows.

First, corrosion rate values from the CORRATOR (mpy, mils (¹/₁₀₀₀'s of an inch) per year metal loss per year) are integrated with respect to time over an interval of from about i to about m, where i equals the baseline corrosion rate at time i and m equals the maximum corrosion rate increase at time m. This integrated value will be referred to as integral 1.

Next, fouling factor is integrated with respect to time over an interval of from about i to about f, where i equals a baseline fouling factor at time i and f equals the fouling factor increase over the baseline by about 20 to about 50 units at time f. This integrated value will be referred to as integral 2. The fouling factor is a value with units HR°F(ft)²/BTU×10⁻⁵ (Hours degree fahrenheit square foot per British Thermal Unit or the Inverse of Conductivity). The section VARIABLES AND EQUATIONS, below, details the calculation of fouling factor. In the equations, fouling factor (FF) is defined by the formula:

$$FF=[1/U_F-1/U_c].$$

In this formula, $U_F$ is a coefficient for heat transfer in a fouled surface and $U_c$ is a coefficient for heat transfer in a clean surface. The section entitled VARIABLES AND EQUATIONS, below, further details the calculation of these coefficients and other variables and equations.

Through operation of continuous monitoring equipment, baseline corrosion rates and fouling factors inherent to the system may be obtained. By utilizing a common start time scan in which corrosion begins to rise above the baseline, integrals 1 and 2 can be compared. Specific graphs have been found to have similar trends to FIG. 1.

Microbiological fouling has been detected when the integral over the interval from about $t_i$ to about $t_f$ ($\Delta t_f$ equals an integral of the time to fouling from the onset of corrosion increase at time $t_i$) is greater than or equal to about 1.4x, where x is defined as the value of the integral over the interval of from about $t_i$ to about $t_m$ ($t_m$ is the time to maximum corrosion change after the establishment of a baseline corrosion rate). Examples are provided in Table 1.

TABLE 1

| | | Example 1 | | | |
|---|---|---|---|---|---|
| | | System | | | |
| Integral | Δt | C | CA-2-4 | CA-3-0 | CA-2-6 |
| 1 | $t_i$ to $t_m$ | 2.5 days | 8 hours | 12 hours | 16 hours |
| 2 | $t_i$ to $t_f$ | 4 days | 24 hours | 36 hours | 24 hours |

Figure 2:
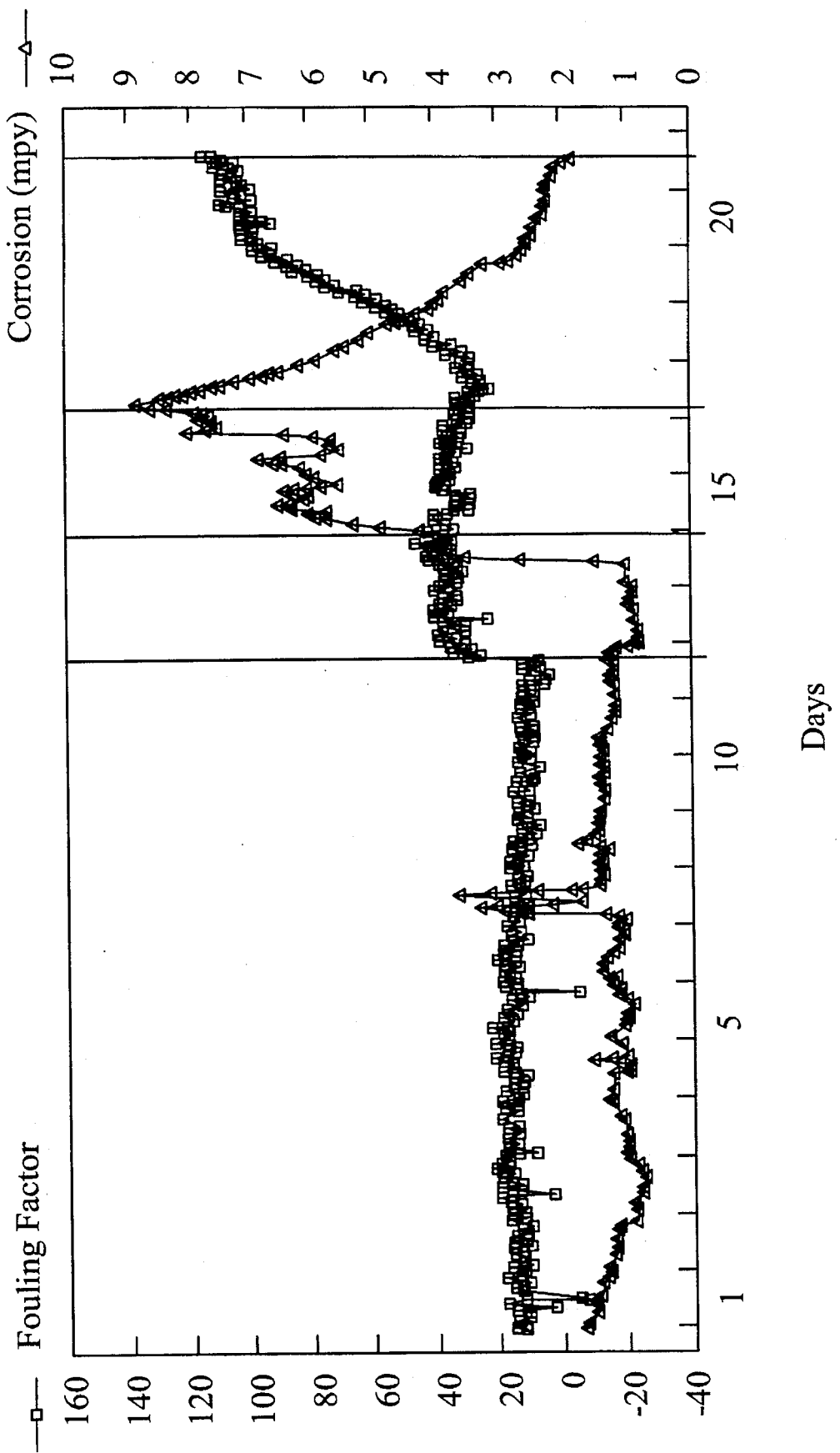
FIG. 2 represents a graph showing fouling factor and corrosion rate with respect to time.
Figure 3:
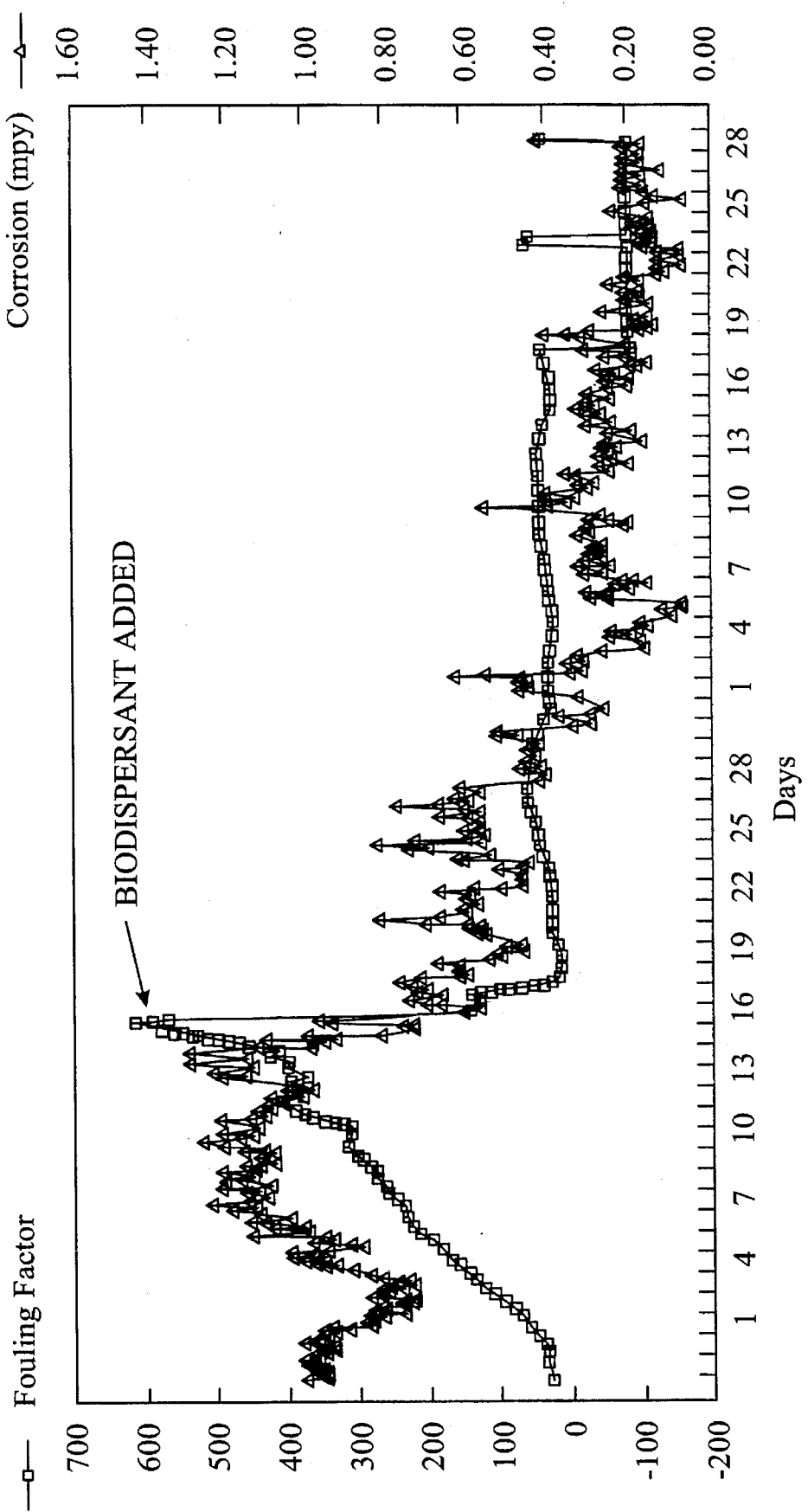
FIG. 3 represents a graph showing fouling factor and corrosion with respect to time and effects of a biodispersant addition.
Figure 4:
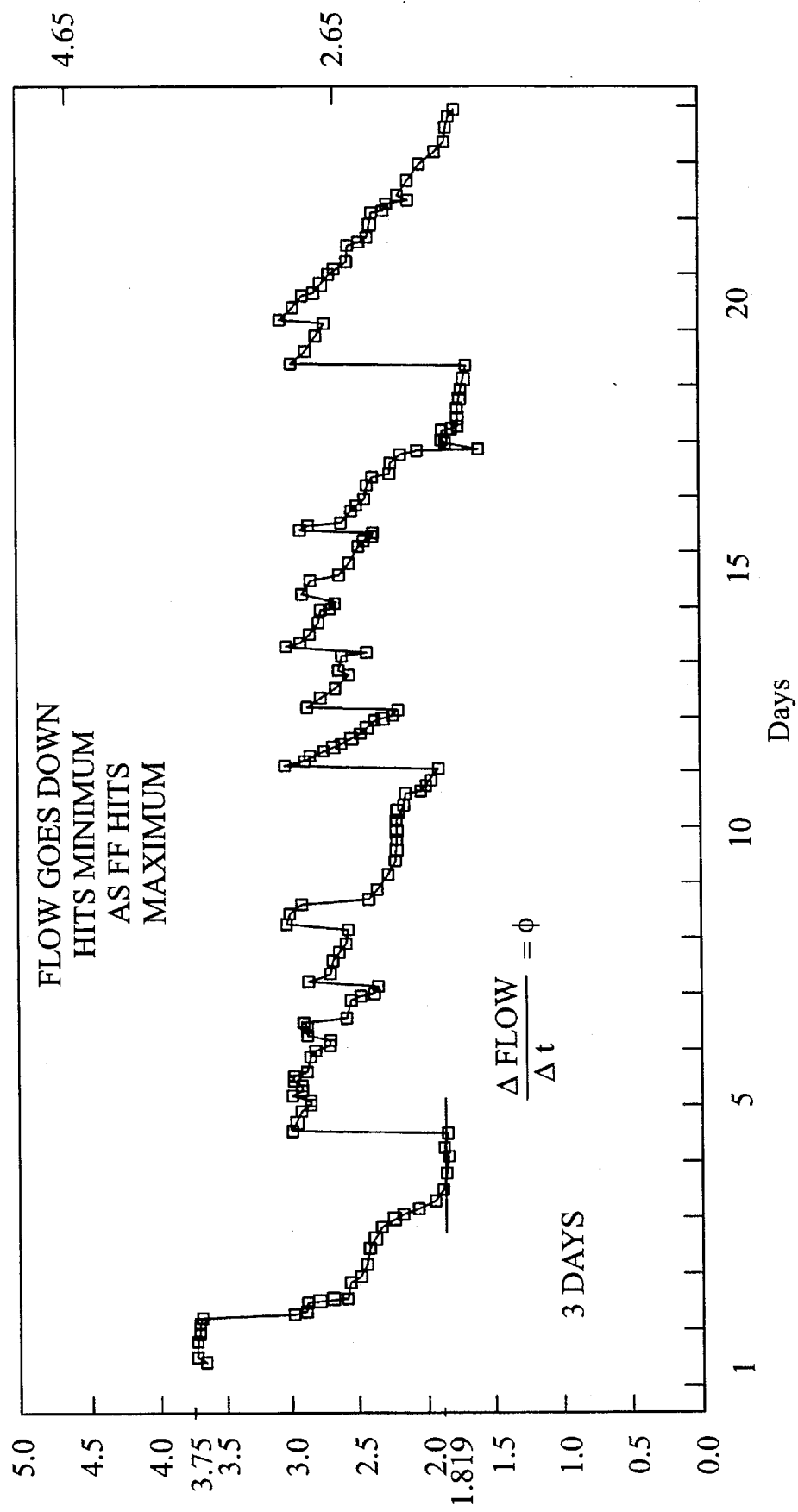
FIG. 4 represents a graph showing flow across the heated test section with respect to time as biological fouling occurs.

The above analysis of the data, which may be provided by the previously disclosed apparatus, allows the present invention to differentiate between microbiological fouling and other types of fouling. FIGS. 2–4 provide graphical data used to develop the method of analysis of the present invention as used as control of microbial fouling or biofilm detection using the previously disclosed apparatus. The data represented by the graphs in FIGS. 2–4 were taken over about a two month period as indicated by the horizontal axis. Various measurements were taken over these time periods, as represented by the vertical axes of the graphs.

In FIG. 3, the fouling and the corrosion drop significantly after a biodispersant is added. FIG. 4 shows how dramatically the flow drops off as the fouling proceeds. FIG. 2 represents a system unchecked by microbicides in order to determine the course of the fouling and its effect on the aqueous system.

The larger the microbiological fouling potential of the cooling water, and/or the lower the linear velocity of a critical heat exchanger, the faster the rate of fouling and, hence, the faster the detection of the microbiological fouling in the present invention.

The two integrals may be further generalized to relative units rather that absolute days. Hence, integral 2, over the interval of from about $t_i$ to about $t_f$ ($\Delta t_f$), can be any units of time. For instance, the units can be minutes, hours, days, with one lower limit restriction to assure that the fouling is microbiological in nature. The lower limit of integral 2, ($\Delta t_f$), is set by laboratory work at from about two hours to about two days, based on the data shown in FIG. 2 and Table 3. Any value below this limit is probably due to organic contamination from foreign sources unless the corrosion rates are not affected. Foreign sources could be, for example, process leaks or fugitive injection of organic matter, that is, failure of hydraulic gear boxes, and the like. Where corrosion rate does not change, the fouling is probably non-viable inorganic and/or mineral deposition in nature.

The calculated $\Delta t_f$ verifies that the fouling is microbiological. Therefore, for simplicity and much more rapid detection of biofilms, the $\Delta t_f$ lower limit will be about 2 hours to about 2 days ($\Delta t_f$) times 1.4.

Once the fouling is determined to be microbiological in nature, the present invention may include steps to control and/or eliminate the responsible microorganisms. Such steps may include altering the chemical and/or physical environment within the system to create an environment unfavorable to the organisms. Such physical changes to the environment may include thermal shocks and/or altering the pH of the system.

Also, the steps may include adding compounds that have a biocidal effect into the aqueous system. Further, the method may include adding growth inhibitors, biodispersants, non-oxidizers, oxidizers, and/or other compounds to the system. Any other known treatment may also be used according to methods of the present invention.

EXAMPLE 1

Loss of Microbiological Control of Biofilms and Corrosion

A reduction in cooling efficiency of a gas heat exchanger and subsequent increase of overall corrosion rates of both mild steel and brass coupons prompted the use of on-line detection equipment. The historical cooling water and treatment parameters for this location are itemized below in Table 2.

TABLE 2

| | |
|---|---|
| Cycles of Concentration | 6.5 |
| pH | 8.3 |
| LSI | 1.5 |
| Total Hardness as $CaCO_3$ | 670 ppm |
| Calcium Hardness as $CaCO_3$ | 450 ppm |
| Total Alkalinity as $CaCO_3$ | 190 ppm |
| Sulfate as $SO_4$ | 370 ppm |
| Silica as $SiO_2$ | 8.8 ppm |
| Chloride as Cl | 103 ppm |
| Conductivity | 1270 μS |
| Mild Steel | 1–2 mpy no under deposit corrosion (U.D.C.) |
| Apparent Retention Time (ART)[4] | 4.3 days |
| half-life[5] | 3.0 days |
| Exchanger Velocity | |
| design | 5.93 ft/sec |
| actual | 2.38 ft/sec |
| Heat flux | 14,270 Btu/hr · $ft^2$ |
| Skin temperature (calc) | 105° F. |
| Aerobic Bacteria | 10,000 CFU/ml |
| All organic | Corrosion/Deposit Control |
| Sulfuric acid | Alk. Reduction |
| Continuous Chlorination | 1.5 ppm F.A.C. |
| Isothiazoline | 1.5 ppm once/month |

[4] $ART = \frac{\text{system liquid holding volume (gallons)}}{\text{system liquid losses (gallons per hour)}}$
[5] Half-life is the time for one-half of the original concentration of an additive remains. The concentration reduction is due to liquid losses from the system and subsequent natural dilution.
Half-life = 0.7 × ART On-line monitoring revealed that at design velocities the mild steel corrosion rates were equivalent to those on historical coupons of 0.8 mpy while the fouling factors were a nominal 30 hr°F(ft)$^2$/Btu×10$^{-5}$. Further investigation was done and it was found that the actual exchanger velocity was 2.38 ft/sec not 5.93 ft/sec. The monitoring equipment was then reset to a velocity of 2.93 ft/sec. At this setting the mild steel corrosion rate began to rise within 2 days and peak at 9 mpy on the 4.5$^{th}$ day while the fouling factor rise lagged behind by approximately 5 days. Colonization took 2 days and a complete microbiological matrix was in place by 5 days, while fouling rose to 620 hr°F(ft)$^2$/Btu×10$^{-5}$ within 14 days or 9 days after maximum corrosion.

Due to the lag in fouling an inorganic dispersant was added to react to the corrosion increase. The corrosion rate dropped to 1.1 mpy while fouling peaked. Subsequent addition of a biodispersant resulted in foulant clean up lowering fouling factor to 30 hr°F(ft)$^2$/Btu×10$^{-5}$ and the corrosion rates to about 0.3 mpy.

Upon CORRATOR electrode inspection, and particularly CORRATOR electrode tip inspection, after this clean up it was apparent that under deposit corrosion damage had been done. The on-line monitoring graphics of fouling, flow and corrosion are illustrated in FIGS. 2 and 3.

The microbiological activity was also tracked and the results are illustrated in Table 3, in Appendix A. The bulk water, at the beginning of the monitoring period, had revealed a total aerobic plate count of 1.3×10$^6$ Colony Forming Units per milliliter (CFU/ml) and an anaerobic plate count of 3040 CFU/ml. Chlorine, isothiazoline, glutaraldehyde and a diamine quat were subjected to these cultures for efficacy. All microbicides were efficacious, that is, a 99.9%–100% population reduction occurred at low dosages to all samples except the heater rod monitor washings.

Even chlorine at 5 ppm, free available chlorine (F.A.C.) did not reduce the populations. Hence, a biodispersant was chosen to reduce the fouling. The heater rod and CORRATOR tip deposits and the results are reported below in Table 4.

TABLE 4

| | CORRATOR Tips | Test Section Rod Washing |
|---|---|---|
| Calcium (as $CaCO_3$) | 22.7% | 30.9% |
| Magnesium (as $CaCO_3$) | 0.4% | 7.3% |
| Iron (as $Fe_2O_3$) | 39.5% | 0.9% |
| Copper (as $Cu_2O$) | 0.2% | 0.2% |
| Zinc (as ZnO) | 0.8% | 2.1% |
| Total Phosphate (as $P_7O_5$) | 12.0% | 21.5% |
| Loss on ignition 550° C. | 13.8% | 25.7% |
| Carbonate (as $CO_2$) | 9.6% | 5.7% |
| Sulfate (as $SO_4$) | <0.1% | <0.1% |
| Acid insoluble silica (as $SiO_2$) | — | (2.8%) 1.9% |
| Moisture Content | (48.3%) | (89.4%) |
| Totals | 99.8% | 96.2% |
| Most Probable Combinations | | |
| Mineral Formulae | | |
| Calcite $CaCO_3$ | 21.8% | 9.5% |
| Hydroxyapatite $Ca_{10}(OH)_2(PO_4)_6$ | 20.9% | 39.1% |
| Munsonite $Mg_2(PO_4)Mg(OH)_2$ | 0.2% | 11.2% |
| Serpentine MgO $SiO_2$ $H_2O$ | | 2.8% |
| Brucite $Mg(OH)_2$ | 0.4% | 8.7% |
| Zinc hydroxide $Zn(OH)_2$ | 1.0% | 2.6% |
| Hematite $Fe_2O_3$ | 39.5% | 1.0% |
| Cupric Oxide $Cu_2O$ | 0.2% | 0.2% |
| Loss on ignition 550° C. | 13.1% | 20.7% |
| Moisture Content | (48.3%) | (89.4%) |
| Totals | 97.1 | 95.8% |

Conclusions of the microbiological fouling detection trial can be summarized as follows:

1) The biofilm building process can be broken out into the following stages:
   Colonization—2 days
   Minimum Fouling Biofilm—5 days
   Maximum Biofilm Growth—14 days
   Maximum Corrosion—5 days—3 days after colonization
   Maximum Corrosion Reduction—5–7 days to higher than base line
   Recolonization after washing—2 hours.
2) The visual appearance of the mild steel coupons and CORRATOR tips are indicative of the fact that once U.D.C. is started, it is irreversible.

Also, in view of the trial conducted in this example as described above, it can be seen that heater rod section effluent flow may be measured to determine whether fouling is microbiological in nature.

EXAMPLE 2

An air conditioning condenser cooling system having an apparent retention time of 92.4 hours (3.85 days) and a half-life of 64.7 hours (2.7 days) at three cycles of concentration was observed to loose biofouling control. The shock addition rate of 2.25 ppm active isothiazoline followed by shock additives every three days, that is, close to system half-life, of 1.125 ppm active isothiazoline maintained the fouling factor at about $100 hr°F(ft)^2/Btu \times 10^{-5}$. Lowering the isothiazoline biocide dosage to 1.125 ppm active initially and following it up by a weekly addition of 1.125 ppm active, just greater than one apparent retention time, that is, 102 hours, resulted in fouling factor increases to 300 $hr°F(ft)^2/Btu \times 10^{-5}$.

The heater rod foulant was found to contain 90% moisture, microorganisms, and a dried analysis revealed 27% loss on ignition, that is, organics, as well as inorganics derived from the recirculating water. Black tubercles were also present on the heater rod and upon addition of hydrochloric acid produced hydrogen sulfide release. The fouling was biological in nature. Also of interest was the fact that after the heater rod was mechanically cleaned and reinstalled, the time to peak fouling was 28 to 36 hours.

Example of System Logic

Figure 5:
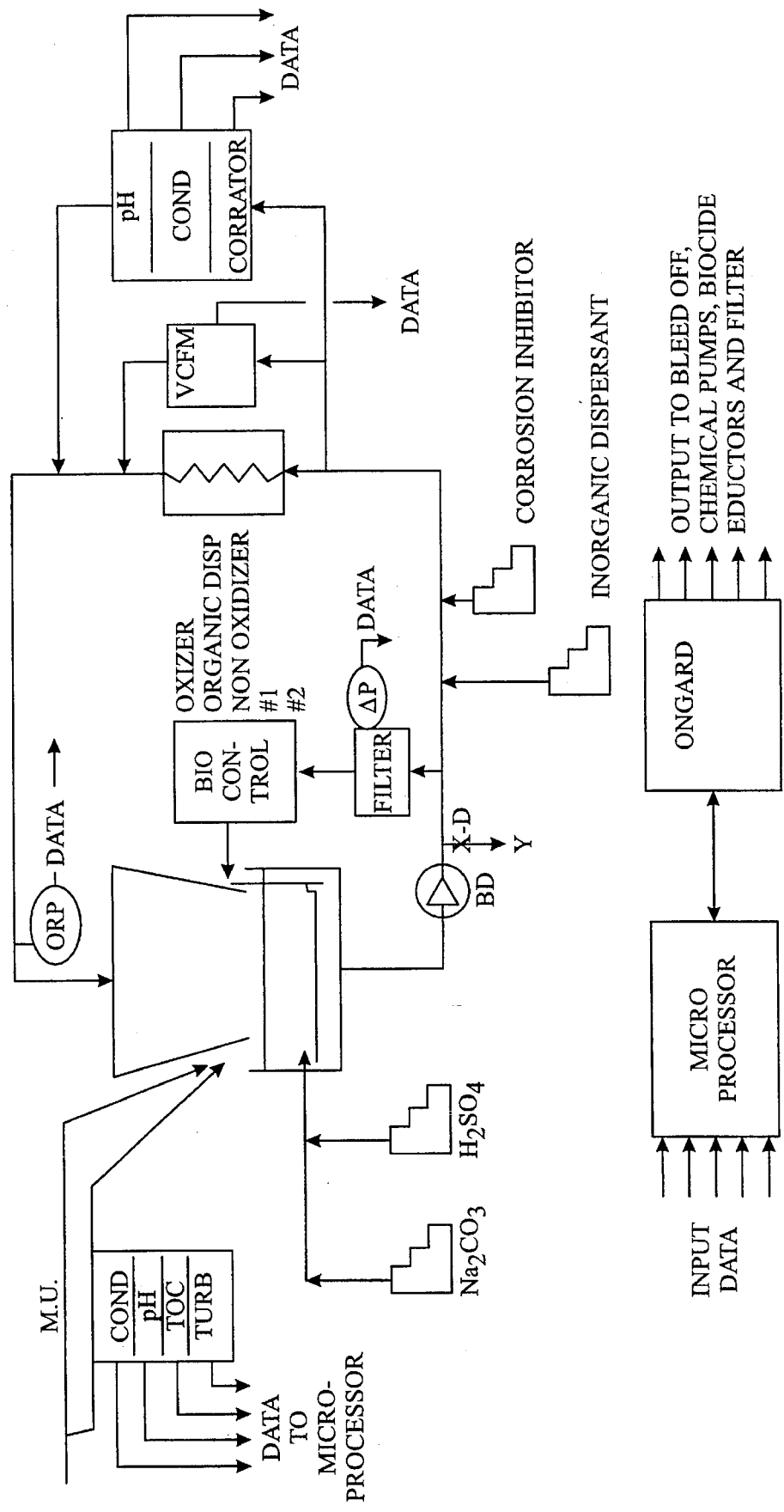
FIGS. 5 and 6 represent a schematic diagram of a system according to the present invention for detecting and controlling microbiological fouling.
Figure 6:
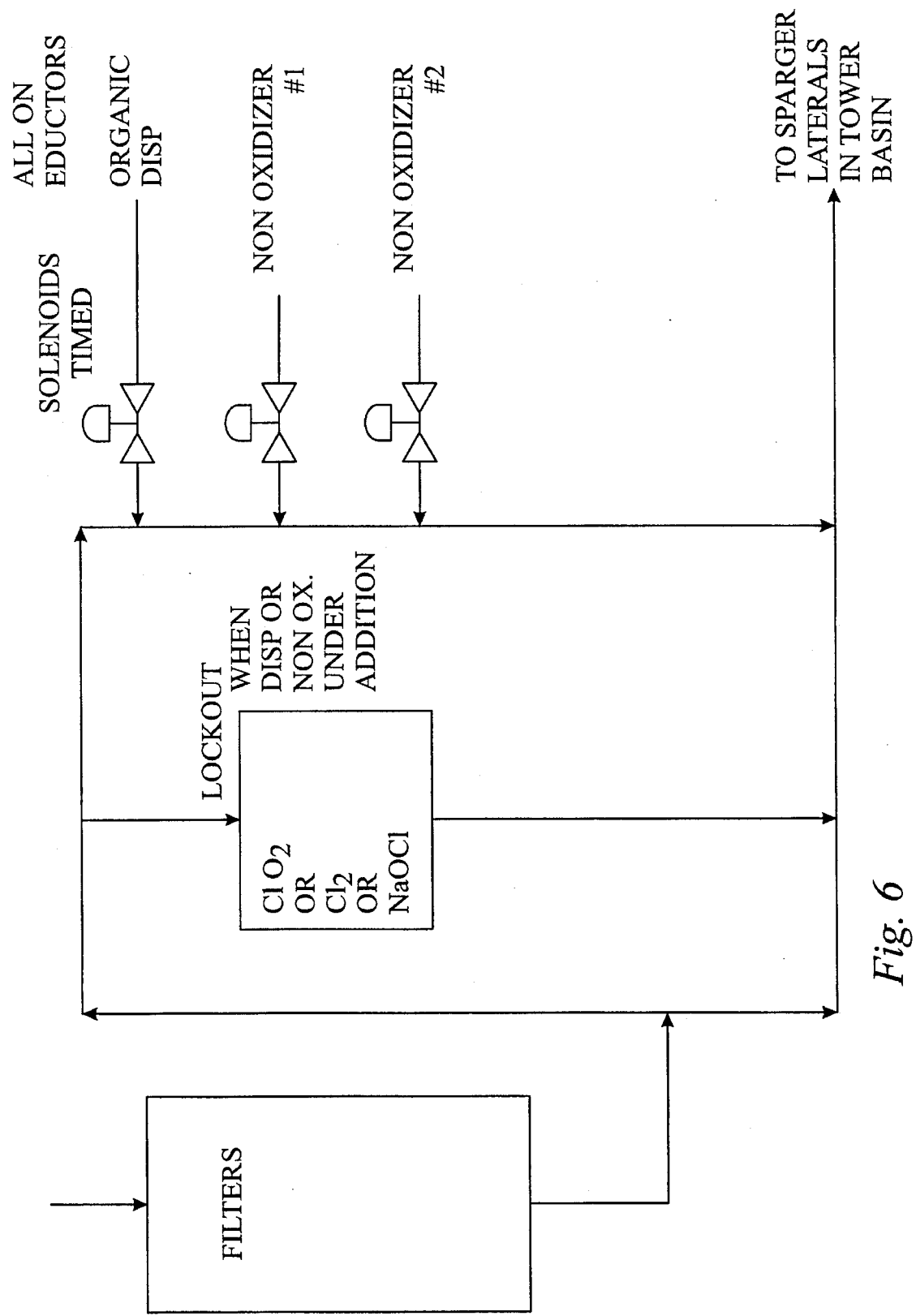

The following represents one embodiment of a generalized logic matrix and is by no means the prototype but rather a springboard to be used to harness feed equipment, detection equipment, computerization, software and SPC in which artificial intelligence can be applied. A generalized layout is illustrated in FIGS. 5 and 6.

| Input Data | Output |
|---|---|
| 1) Case 1 | |
| M.U. TURB-P | 1) INCREASE INORGANIC DISPERSANT IN |
| M.U. pH-G | INCREMENTS OF 10 PPM ÷ ONGARD |
| M.U. TOC-G | CYCLES |
| M.U. COND-G | |
| CWT FF-P | 2) BACKWASH FILTER AT SETPOINT ΔP- |
| CWT MPY-G→P | 2 PSIG |
| CWT FILTER ΔP-G→P | |
| CWT pH-G | 3) INCREASE BLEED OFF WHEN AND TO HOLD |
| CWT COND-G | $C_{DESIRED} = \frac{\text{SPECIFIED CWT T.S.S.}}{\text{M.U. T.S.S.}}$ |
| CWT ORP-G | |
| CWT TRACER-G | (PID) CONTROL TRIM) |
| | 4) CHECK MAKE UP TREATMENT PLANT |
| Case 2 | |
| M.U. TURB-P | 1) INCREASE OXIDIZER (PID) |
| M.U. pH-P⊕ | 2) SLUG FEED (EDUCTOR) ORGANIC |
| M.U. TOC-P | DISPERSANT AT 50 ppm, THEN 50 ppm AT |
| M.U. COND-G | t½ IF FF STILL POOR. |
| CWT pH-G | |
| CWT COND-G | 3) IF ORP TRENDING P→G BUT FF/MPY |
| CWT TRACER-G | TREND STILL NOT IMPROVED BY t½ |
| CWT FILTER ΔP-G | AFTER STEP 2 THEN ADD NON OXIDIZER |
| CWT FF-P | SINCE pH⊕↑ IN M.U. FROM RECYCLE |
| CWT ORP-G→P | WASTE $NH_3$ THEN B.S.250 IS ADDED OVER |
| CWT MPY-G→P | B.S.254 |
| | 4) CHECK WASTE SYSTEM CLARIFICATION |

G = good results, within control range
P = poor results, outside of control range
M.U. = make up water
CWT = cool water
FF = fouling factor
TURB = turbidity
pH = log $[H]^+$
COND = conductivity
TOC = total organic carbon
MPY = corrosion rate in mils per year
ORP = oxidation reduction potential
Filter ΔP = pressure differential across the filter
Tracer = a testable of the deposit and corrosion control inhibitor added to the system

VARIABLES AND EQUATIONS

Fouling Factors

| | Nomenclature | Units of Measurement | |
|---|---|---|---|
| | | Metric | English |
| A | Area | $m^2$ | $ft^2$ |
| C | Constant (dimensionless) | | |
| CF | Cleanliness factor (dimensionless) | | |
| $C_p$ | Heat capacity | cal/g-°C. | BTU/lb-°F. |
| D | Pipe Diameter | m | ft |
| f | Friction factor (dimensionless) = $4 f_r$ | | |
| $f_r$ | Fanning friction factor (dimensionless) | | |
| g | Acceleration of gravity | 9.8 m/s$^2$ | 32.2 ft/s$^2$ |
| $h_1$ | Friction loss (pressure drop) | m (of head) | ft (of head) |
| L | Pipe length | m | ft |
| LMTD | Log mean temperature difference$^{(A)}$ (countercurrent flow) $[(t_1 - T_2) - (t_2 - T_1)]/\ln[(t_1 - T_2) - (t_2 - T_1)]$ | °C. | °F. |
| m | Mass flow | kg/h | lb/h |
| ΔP | Pressure drop (head) | m | ft |
| q | Heat input or heat duty | w | BTU/h |
| $R_w$ | Thermal resistance of wall | (°C.)/W | (h)(°F.)/BTU |
| $R_d$ | Thermal resistance of deposit (fouling factor) | (°C.)/W | (h)(°F.)/BTU |
| $R_f$ | Thermal resistance of water film | (°C.)/W | (h)(°F.)/BTU |
| Re | Reynolds number (dimensionless) | | |
| $r_1$ | Outer radius of inner tube | m | ft |
| $r_2$ | Inner radius of outer tube | m | ft |
| $r_{max}$ | Hydraulic radius | m | ft |
| $T_1$ | Cooling water inlet temperature | °C. | °F. |
| $T_2$ | Cooling water outlet temperature | °C. | °F. |
| $T_b$ | Bulk water temperature: Temperature of water entering fouling monitor | °C. | °F. |
| $T_s$ | Temperature of heat exchange surface | °C. | °F. |
| $T_w$ | Temperature of wall between heat source and heat exchange surface | °C. | °F. |
| $t_1$ | Process inlet temperature | °C. | °F. |
| $t_2$ | Process outlet temperature | °C. | °F. |
| U | Overall heat transfer coefficient | W/m$^2$-°C. | BTU/H-ft$^2$-°F. |
| V | Mean fluid velocity of flow | m/s | ft/s |
| ρ | Fluid density | kg/m$^3$ | lb/ft$^3$ |
| $\tau_1$ | Shear stress on surface of inner tube | kg$_F$/m$^2$ | lb$_F$/ft$^3$ |
| $\tau_2$ | Shear stress on inner surface of outer tube | kg$_F$/m$^2$ | lb$_F$/ft$^3$ |

Figure 8A:
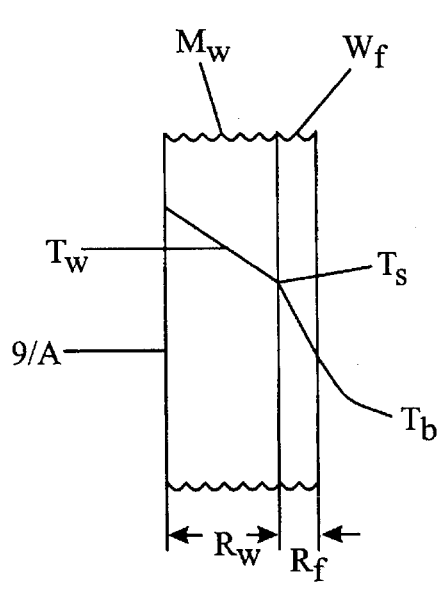
FIG. 8a represents a schematic diagram of a temperature profile of a clean tube.
Figure 8B:
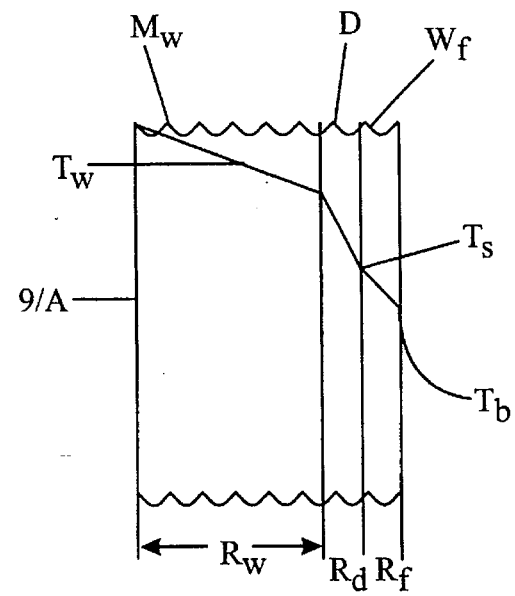
FIG. 8b represents a schematic diagram of a temperature profile deposit-fouled tube.

Subscripts:
b=Bulk fluid
c=Clean conditions
d=Fouled conditions/deposit
f=Water film
F=Force
o=Design conditions
s=Surface
w=Wall The following equations are basic heat transfer algorithms that are applicable to fouling analysis. In interpreting these equations, the above-listed variables as well as FIGS. 8a and 8b may be made reference to. FIGS. 8a and 8b show schematic diagrams of a temperature profile of a clean and a deposit-fouled tube, respectively. The variables shown in FIGS. 8a and 8b are defined above. In addition, Mw represents a metal wall of a tube, Wf represents a water film adjacent the tube wall, and D represents a deposit on the tube wall.

For a process heat exchanger:

$$U=(q/A)/LMTD$$

For a fouling monitor:

$$U=(q/A)/(T_w-T_b)$$

$$UA=1/(R_w+R_d+R_f)$$

$$U=(m/A)(T_2-T_m)\,(Cp)/LMTD, \text{ for water, } C_p=1$$

For a clean heat exchange surface:

$$(T_s)_c=(T_w)_c-[(q)_c(R_w)]$$

$$(R_f)_c=[(T_s)_c-(T_b)_c]/(q)_c$$

For a fouled heat exchange surface:

$$(T_s)_d = (T_b)_d + (q)_d (R_f)_d$$

$$R_d = [(T_w)_d - (T_s)_d]/(q)_d = R_w$$

TABLE 3

| | MICROBIOLOGICAL SCAN | | | |
|---|---|---|---|---|
| | BULK WATER | | | |
| | BEFORE SHUT DOWN | DURING SHUT DOWN | MONITOR CLEANING | 2 HRS AFTER CLEANING |
| TAB CFU/ml | $1.3 \times 10^6$ | $6.0 \times 10^6$ | $164 \times 10^6$ | $1.0 \times 10^6$ |
| Bacteria/gm dry wt | | | $1.6 \times 10^9$ | |
| Bacteria/gm (wet wt) | | | $1.7 \times 10^8$ | |
| IRON BACTERIA | | YES | YES | |
| SRB's CFU/ml | | $1.0 \times 10^5$ | $1.5 \times 10^6$ | |
| Bacterial ID | *Corynebacterium aquatium* AEROBE $3.25 \times 10^5$ *Flavobacterium* AEROBE $7.8 \times 10^5$ *B. cereus* FAC. AN. $1.95 \times 10^5$ | *Corynebacterium aquatium* AEROBE $9 \times 10^5$ *Flavobacterium* AEROBE $2.2 \times 10^6$ *B. cereus* FAC. AN. $2.9 \times 10^6$ | *Corynebacterium aquatium* AEROBE $1.9 \times 10^7$ *Flavobacterium* AEROBE $5.6 \times 10^7$ *B. cereus* FAC. AN. $5.6 \times 10^7$ *Pseudomonas acidovarans* AEROBE $5.6 \times 10^7$ $4.0 \times 10^6$ | *Corynebacterium aquatium* AEROBE $2 \times 10^5$ *Flavobacterium* AEROBE $2 \times 10^5$ *B. cereus* FAC. AN. $6 \times 10^5$ |

If $q/A$, $T_b$, and $R_f$ remain constant during a fouling run, then $R_d$ (fouling factor) may be calculated:

$$R_d = [(T_w)_d - (T_w)_c]/(q)$$

A cleanliness factor may be determined:

$$CF, U_d/U_o$$

If $U_o$ is not known, it may be calculated:

$$U_o = 1/[(1/U_c) + AR_d]$$

The general equation for pressure-drop determination, also known as the Darcy-Weisbach equation, is:

$$h_f = \Delta P = (fLV^2)/(2Dg)$$

The following equations define shear stress:

$$f = 0.079 Re^{-0.25}$$

$$T_2 = f\rho V^2/2g$$

$$r_{max}^2 = (r_2^2 - r_1^2)/\ln(r_2/r_1)^2$$

$$\tau_1 = \tau_2(r_2/r_1)(r_{max}^2 r_1^2)/(r_2^2 - r_{max}^2)$$

Although the above-described process and apparatus provides for on-line corrosion monitoring, other processes and apparatus may be employed. In fact, any process and apparatus that permits measurement variables necessary to determine whether the fouling is biological may be employed. Preferably, the apparatus and method may be used that produce a reproducible corrosion rate.

In this disclosure, there is shown and described only the preferred embodiments of the invention, but, as aforementioned it is to be understood that the invention is capable of use in various other combinations and environments and is capable of changes or modifications within the scope of the inventive concept as expressed herein.

What is claimed is:

1. A method of detecting microbiological fouling in an aqueous system, said method comprising the steps of:
   a) determining a baseline corrosion rate;
   b) continuously measuring corrosion rate;
   c) measuring a change in said corrosion rate;
   d) measuring a maximum corrosion rate;
   e) determining a baseline fouling factor by measuring and monitoring parameters of a fluid in said aqueous system;
   f) determining an increase in fouling factor over the baseline;
   g) integrating a change in said corrosion rate with respect to time over an interval of from a time of said determination of said baseline corrosion rate to a time that said maximum corrosion rate occurs;
   h) integrating change in said fouling factor with respect to time over an interval from a time of a said determination of said baseline fouling factor to a time of said determination of said increase in fouling factor; and
   i) comparing said fouling factor and said corrosion rate to determine if said fouling is microbiological.

2. A method according to claim 1, wherein said baseline corrosion rate is determined by utilizing linear polarization resistance.

3. A method according to claim 1, wherein said corrosion rate is measured utilizing linear polarization resistance.

4. A method according to claim 1, wherein said change in said corrosion rate is measured utilizing linear polarization resistance.

5. A method according to claim 1, wherein said maximum corrosion rate is measured utilizing linear polarization resistance.

6. A method according to claim 1, wherein said corrosion is integrated over an interval of from about $t_i$ to about $t_m$, wherein $t_m$ is a time to a maximum corrosion after the establishing of a baseline corrosion rate.

7. A method according to claim 1, wherein said fouling factor in integrated over an interval of from about $t_i$ to about $t_f$, wherein $\Delta t_f$ is an integral of time to fouling from an onset of a corrosion increase from a baseline value at $t_i$.

8. A method according to claim 1, wherein said corrosion is integrated over an interval of from about $t_i$ to about $t_m$, wherein $t_m$ is a time to corrosion change from said baseline level and said fouling factor is integrated over an interval of from about $t_i$ to about $t_f$, wherein $\Delta t_f$ is a time to fouling increase upon corrosion change from baseline values, said fouling is microbiological if said integration of said fouling factor produces a value greater than or equal to about 1.4 times the value produced by integration of said corrosion.

9. A method according to claim 1, wherein said baseline fouling factor is determined according to the formula:

Fouling Factor=$[1/U_F - 1/U_c]$, wherein $U_F$ is a coefficient for heat transfer in a fouled surface and $U_c$ is a coefficient for heat transfer in a clean surface.

10. A method according to claim 1, wherein said parameters comprise linear polarization resistance and fouling factors.

11. A method of detecting and controlling microbiological fouling in an aqueous system, said method comprising the steps of:

a) determining a baseline corrosion rate;

b) continuously measuring corrosion rate;

c) measuring a change in said corrosion rate;

d) measuring a maximum corrosion rate;

e) determining a baseline fouling factor by measuring and monitoring parameters of a fluid in said aqueous system;

f) determining an increase in fouling factor over the baseline;

g) integrating a change in said corrosion rate with respect to time over an interval of from a time of said determination of said baseline corrosion rate to a time that said maximum corrosion rate occurs;

h) integrating change in said fouling factor with respect to time over an interval from a time of a said determination of said baseline fouling factor to a time of said determination of said increase in fouling factor;

i) comparing said fouling factor and said corrosion rate to determine if said fouling is microbiological; and j) administering a treatment to the aqueous system, said treatment including at least one member being selected from the group consisting of adding an effective amount of at least one compound having a biocidal effect, and altering the physical environment within the aqueous system to create conditions unfavorable to the organisms involved in the fouling.

12. A method according to claim 11, wherein said baseline corrosion rate, said corrosion rate, said change in said corrosion rate, and said maximum corrosion rate are determined or measured by utilizing linear polarization resistance in said aqueous system.

13. A method according to claim 11, wherein said corrosion is integrated over an interval of from about $t_i$ to about $t_m$, wherein $t_m$ is a time to corrosion change from said baseline level.

14. A method according to claim 11, wherein said fouling factor is integrated over an interval of from about $t_i$ to about $t_f$, wherein $\Delta t_f$ is a time to fouling increase upon corrosion change from baseline values.

15. A method according to claim 11, wherein said corrosion is integrated over an interval of from about $t_i$ to about $t_m$, wherein $t_m$ is a time to corrosion change from said baseline level and said fouling factor is integrated over an interval of from about $t_i$ to about $t_f$, wherein $\Delta t_f$ is a time to fouling increase upon corrosion change from baseline values, said fouling is microbiological if said integration of said fouling factor produces a value greater than or equal to about 1.4 times the value produced by integration of said corrosion.

16. A method according to claim 11, wherein said baseline fouling factor is determined according to the formula:

Fouling Factor=$[1/U_F - 1/U_c]$, wherein $U_F$ is a coefficient for heat transfer in a fouled surface and $U_c$ is a coefficient for heat transfer in a clean surface.

17. A method according to claim 11, wherein said parameters comprise linear polarization resistance and fouling factors.

18. A method according to claim 11, further comprising the step of confirming successful treatment of said microbiological fouling by comparing said fouling factor and said corrosion rate after administration of said treatment to the aqueous system.

19. An apparatus for detecting microbiological fouling in an aqueous system, said apparatus comprising:

a) at least one pair of electrodes positioned in the aqueous system;

b) a measurer for measuring current flowing between said electrodes;

c) monitors and measurers for monitoring and measuring conditions within the aqueous system comprising fouling factor and heater rod test section effluent flow; and d) a processor for processing data representing said measured corrosion rates, fouling factors, and heater rod section effluent flow, said processor determining a baseline corrosion rate, continuously measuring corrosion rate, measuring a change in said corrosion rate, measuring a maximum corrosion rate, determining a baseline fouling factor by measuring and monitoring parameters of a fluid in the aqueous system, determining an increase in fouling factor over the baseline, integrating a change in said corrosion rate with respect to time over an interval of from a time of said determination of said baseline corrosion rate to a time that said maximum corrosion rate occurs, integrating change in said fouling factor with respect to time over an interval from a time of a said determination of said baseline fouling factor to a time of said determination of said increase in fouling factor, and comparing said fouling factor and said corrosion rate to determine if said fouling is microbiological.

20. An apparatus according to claim 19, wherein said conditions include linear polarization resistance, fouling factors, and heater rod section effluent flow.

21. An apparatus according to claim 19, further comprising means for measuring oxidation-reduction potential.

* * * * *